Figure 4:
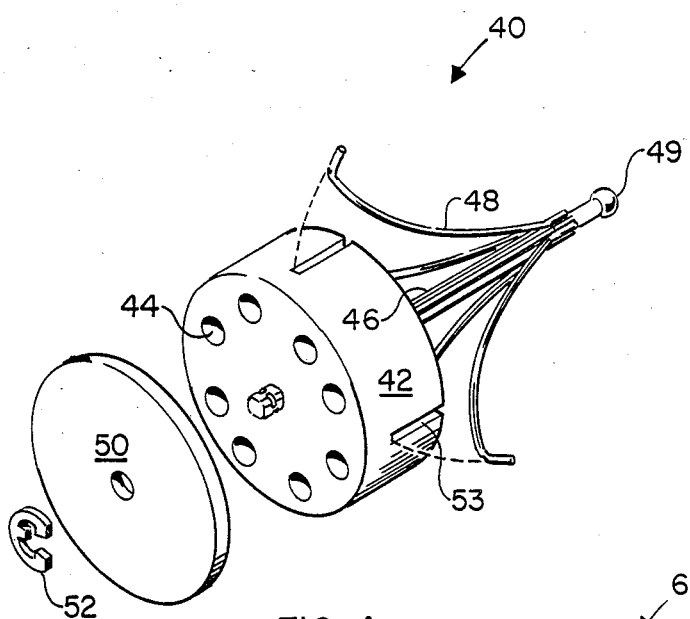

United States Patent [19]  
Colvin et al.

[11] Patent Number: 4,936,823  
[45] Date of Patent: Jun. 26, 1990

[54] TRANSENDOSCOPIC IMPLANT CAPSULE

[75] Inventors: David P. Colvin, Apex, N.C.; Bernard R. Marsh, Upperco, Md.

[73] Assignees: Triangle Research and Development Corp., Raleigh, N.C.; The Johns Hopkins Univ., Baltimore, Md.

[21] Appl. No.: 190,108

[22] Filed: May 4, 1988

[51] Int. Cl.⁵ .............................. A61M 36/12
[52] U.S. Cl. ........................ 600/7; 604/106; 604/107
[58] Field of Search ........... 600/3, 6, 7, 8; 604/57, 604/106, 107; 128/788

[56] References Cited

U.S. PATENT DOCUMENTS

| | | | |
|---|---|---|---|
| 3,323,511 | 6/1967 | Holter | 128/1.2 |
| 4,086,914 | 5/1978 | Moore | 128/1.2 |
| 4,244,357 | 1/1981 | Morrison | 128/1.2 |
| 4,389,208 | 6/1983 | LaVeen et al. | 604/106 |
| 4,402,308 | 9/1983 | Scott | 128/1.2 |
| 4,416,659 | 11/1983 | Simpson et al. | 604/57 |
| 4,461,280 | 7/1984 | Baumgartner | 128/1.2 |
| 4,554,909 | 11/1985 | Torres | 600/6 |
| 4,584,991 | 4/1986 | Tokita et al. | 600/3 |
| 4,588,395 | 5/1986 | Lemelson | 604/59 |
| 4,616,640 | 10/1986 | Kaali et al. | 128/788 |

FOREIGN PATENT DOCUMENTS 857992 1/1961 United Kingdom .

Primary Examiner—Lee S. Cohen  
Assistant Examiner—Krista M. Pfaffle  
Attorney, Agent, or Firm—Richard E. Jenkins

[57] ABSTRACT

An implant capsule for insertion into a body canal to apply radiation treatment to a selected portion of the body canal. The device includes a body member defining at least one therapeutic treatment material receiving chamber and at least one resilient arm member associated with the body member for removably engaging the body canal when the device is positioned therein.

9 Claims, 2 Drawing Sheets

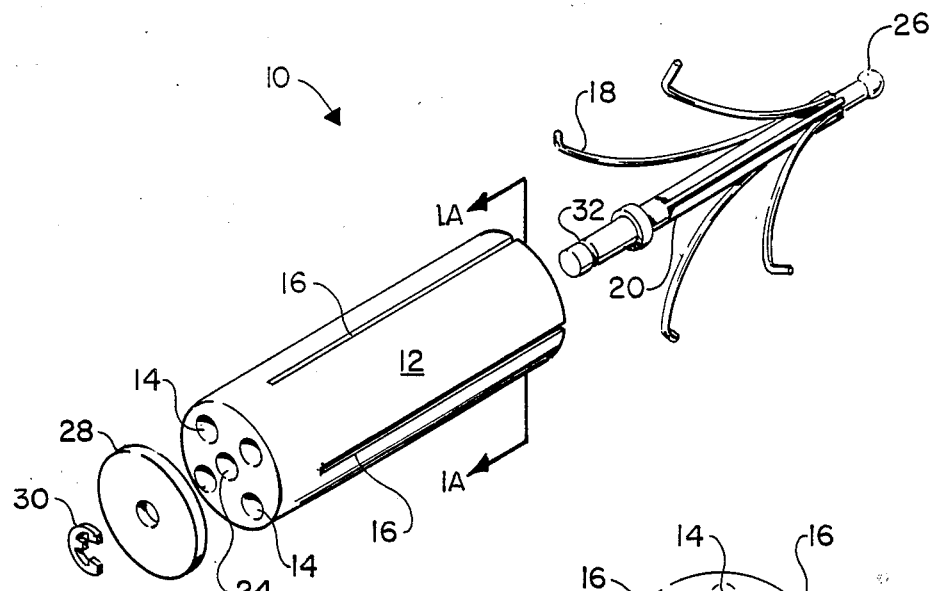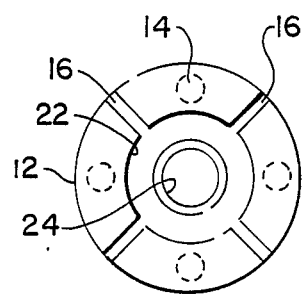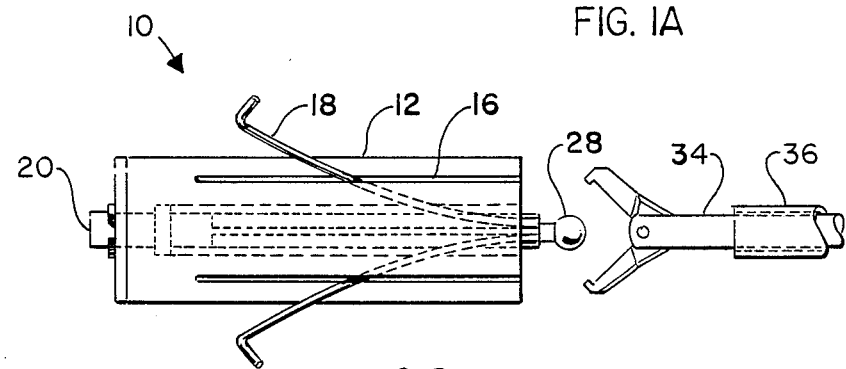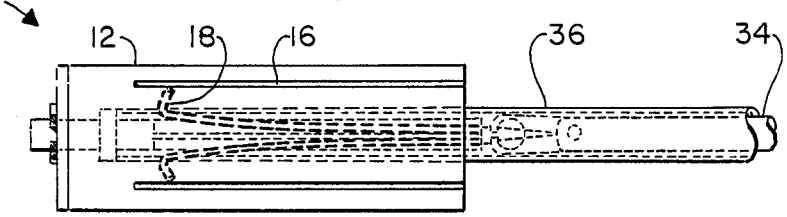

TRANSENDOSCOPIC IMPLANT CAPSULE

TECHNICAL FIELD

The present invention relates to a device for applying a therapeutic treatment to a selected portion of the body and, more particularly, to an improved device for applying therapeutic radiation by being transported into a body orifice via a fiberoptic endoscope to a predetermined portion thereof.

BACKGROUND ART

In the United States there are presently over 100,000 deaths per year resulting from bronchial carcinoma or lung cancer. Conventional treatments for lung cancer include surgery, radiation therapy and chemotherapy. Although the surgical removal of a malignant lung tissue remains as the effective method of choice of physicians, it may only be accomplished in a few early cases before intrathoracic or distant spread of the tumor has taken place. Radiation therapy by external beam has been found to be of limited value in prolonging the life of a patient with the disease even with doses in the range of 5,000 to 6,000 rads in view of the inability to control the irradiated tumor and a high incidence of distant metastases.

Interstitial irradiation has been shown to be promising for the local treatment of certain tumors assuming that the dose rate of radiation delivered from a stereotoxically implanted source is sufficiently high that tumor cells receive a critical threshold dose during a complete cell cycle. This condition can be met by using high-activity radioisotopes which can be removed from the site after the dose is delivered thereto. If the high-activity radioisotope were to remain implanted, normal tissue surrounding the radioactive source would be exposed to potentially toxic doses of radiation. It is known to utilize removable radioactive sources encased within catheters made to precisely hold the radioactive source at the tumor target site. An improvement in this art is disclosed in U.S. Pat. No. 4,584,991 to Tokita, et al.

In view of shortcomings presented by the present state of the radiation therapy art, applicant has developed an inventive implant capsule for radioisotopes which is adapted to be remotely implanted and retrieved by means of a catheter inserted through the collateral lumen of a fiberoptic bronchoscope. The capsule possesses resilient engaging means to enable the implant device to engage the bronchial walls when released at a predetermined location for treatment of a bronchial malignancy. The implant capsule has application to other organs and other types of endoscopes and may also be used for endoscopic drug delivery by placing a chemotherapeutic agent therein for localized or topical chemotherapy treatment.

DISCLOSURE OF THE INVENTION

In accordance with the present invention, applicant provides a transendoscopic implant capsule adapted to be transported through a body cavity or passageway in order to apply a therapeutic radiation or chemotherapeutic treatment to a tumor or a malignant area within the body. The implant capsule comprises a body member defining one or more elongate treatment material receiving chambers therein and one or more resilient arm members cooperatively associated with the body member and extending generally radially outwardly therefrom. In this fashion the arm members may be radially compressed inwardly during transportation of the implant capsule to a selected portion of the body requiring therapeutic treatment and then released in order that the arm members may return to its outwardly extending position in order to engage the body portion and thereby retain the capsule in place.

Accordingly, it is an object of the device of the invention to provide an improved implant capsule of type adapted to contain a radioactive therapeutic treatment for point-source localized radiotherapy.

A further object of the present invention is to provide an implant capsule for application of radiotherapy or chemotherapy treatment which is adapted to be remotely implanted and retrieved with a fiberoptic bronchoscope.

A still further object of the present invention is to provide an implant capsule adapted for containing a selected number of radioisotope seeds for radiotherapy which can be remotely implanted and retrieved with a fiberoptic bronchoscope and which is further adapted to engage the body portion with resilient arms when implanted therein.

BRIEF DESCRIPTION OF THE DRAWINGS

Some of the objects of the invention having been stated, other objects will become evident as the description proceeds, when taken in connection with the accompanying drawings, in which:

FIG. 1 is an exploded perspective view of a preferred embodiment of the implant capsule of the present invention;

FIG. 1A is a view of the body member of the present invention taken along line 1A—1A of FIG. 1;

FIG. 2 is a side elevation view of the implant capsule shown in FIG. 1 with the resilient arm members fully extended;

FIG. 3 is a side elevation of the implant capsule of FIG. 1 with the resilient arm members fully collapsed within the body member thereof;

FIG. 4 is a perspective view of a second embodiment of the implant capsule of the present invention comprising a shortened body member;

FIG. 5 is a perspective view of a third embodiment of the implant capsule of the present invention comprising a shortened body member and a flexible central stem from which the arm members extend; and FIG. 6 is a perspective view of another embodiment of the implant capsule of the present invention wherein the body member comprises a singular flexible elongate chamber.

BEST MODE FOR CARRYING OUT THE INVENTION

Referring now generally to the drawings, several different embodiments of an implant capsule of the present invention are depicted which comprise a body member defining at least one elongate therapeutic treatment material receiving chamber therein to hold radioisotope seeds or a chemotherapeutic agent and resilient arm members to restrain movement of the capsule when properly positioned within the body. The implant capsule's resilient arm members are designed to have maximum stored spring energy per unit length in order to minimize the required size of the capsule when retracted and released using an external catheter and forceps which can be introduced through a fiberoptic bronchoscope. A standard biopsy-type forcep modified to grasp the spherical tip of the stem of the resilient arm members may be utilized within a sheath to retract the resilient arm members by sliding the sheath thereover and later to extend them by removing the sheath. Although the use of a catheter or sheath with a slidably movable biopsy forcep therein is presently contemplated as the preferred type of instrument to manipulate the implant capsule of the present invention, other manipulation means are clearly possible.

Referring now specifically to FIGS. 1-3, there is illustrated a preferred embodiment, generally designated 10, of the implant capsule of the invention for applying therapeutic radiation to a selected portion of the body. Implant capsule 10 consists of body member 12 which defines a plurality of chambers 14 therein adapted to receive a therapeutic treatment material such as radioisotope seeds and/or chemotherapeutic agents. The use of both a radioactive isotope and a chemotherapeutic material is known to have a synergistic effect in the treatment of cancer, and the use of both in capsule 10 may be desirable. Body member 12 also defines a plurality of radially extending slots 16, as best seen in FIGS. 1 and 1A. Resilient arm members 18 are secured to central stem 20 and adapted to be slidably received by the bore 22 (see FIG. 1A) and slots 16 within body member 12. The face of body member 12, as best illustrated in FIG. 1A, illustrates that bore 22 extends along the length of body member 12 and terminates with a relatively small diameter aperture 24 at the remote end thereof. Central stem 20 is received within body member 12 so that the end portion thereof (opposite sphere 26) extends through aperture 24 and cap 28 so that E-clip 30 may be secured to groove 32 of the stem in order to assure a snug fit of body member 12, cap 28 and central stem 20 after a treatment material is placed within chamber 14. Although a matter of design choice, chambers 14 will accommodate up to 28 radioactive isotope units and/or chemotherapeutic agent boluses in the preferred embodiment of the invention illustrated in FIGS. 1-3. Arm members 18 are most suitably fabricated from a special alloy wire (such as MP 35N manufactured by Maryland Specialty Wire Company) having a tensile strength of at least 300,000 psi. and which is compatible with body tissues and fluids. Central stem 20 can be stainless steel or other compatible metal and arm members 18 are attached thereto by a suitable method of fixation such as electric fusion welding. Body member 12 and cap 28 are fabricated from a biocompatible plastic material.

As best seen in FIGS. 2 and 3, in clinical usage a grasping forcep 34 within catheter 36 would be inserted through the collateral lumen at the proximal end of a bronchoscope (not shown) and passed therethrough to engage sphere 26 of implant capsule 10 at the remote or distal end of the bronchoscope. Flexible sheath or catheter 36 is then extended (see FIG. 3) into bore 22 of body member 12 so as to extend over and collapse resilient arm members 18 into slots 16. Implant capsule 10 and catheter 36 positioned in the lumen of the fiberoptic bronchoscope are then inserted into a selected area of the patient's lung. Catheter 36 is retracted so as to permit resilient arm members 18 to extend outwardly through slots 16 and the barbs at the ends thereof to secure the capsule to the inner bronchus wall. With this retrograde-load technique, capsules larger than the accessory lumen can be implanted and retrieved. Once the capsule has been secured, the bronchoscope and associated forcep 34 and catheter 36 are temporarily withdrawn. After a predetermined prescribed treatment time, the bronchoscope is reinserted into the bronchus and the process repeated in order to retract arm members 18 and withdraw implant capsule 10 from its location in a patient's lung.

A second embodiment of the present invention is illustrated in FIG. 4 and generally designated 40. Implant capsule 40 comprises body member 42 defining treatment receiving chambers 44 therein, central stem 46 with resilient arm members 48 and sphere 49, cap 50 and E-clip 52. Arm members 48 are received by slots 53 when collapsed by catheter 36 (see FIG. 2) into body member 42 for insertion or removal from the lung. This embodiment of the invention is substantially similar to that shown in FIGS. 1-3 except body member 42 only extends for a portion of the length of stem 46 and the chambers therein are of a shorter length than chambers 14 of implant capsule 10. Implant capsule 40 is therefore capable of holding fewer isotope seeds, most suitably about 8, and less of other chemotherapeutic agents than is the capsule described hereinbefore.

Figure 5:
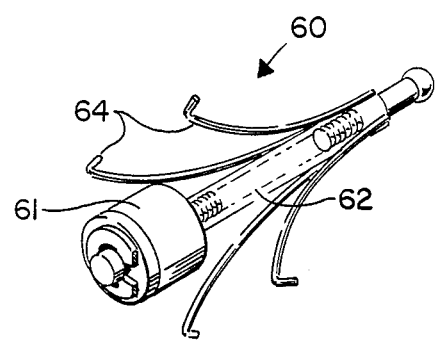

A third embodiment of the present invention is depicted in FIG. 5 and generally designated 60. Implant capsule 60 is similar to implant capsule 40 but additionally provides a flexible central stem 62 to which resilient arm members 64 are attached. Flexible central stem 62 allows for greater ease of manipulation or flexing of implant capsule 60 as it is moved within the lumen of a bronchoscope and can also be used to contain a linear distribution of radioisotope seeds. The body or pod member 61 is smaller and presently contemplated to contain only about 4 radioisotope seeds within the chambers defined therein (not shown).

Figure 6:
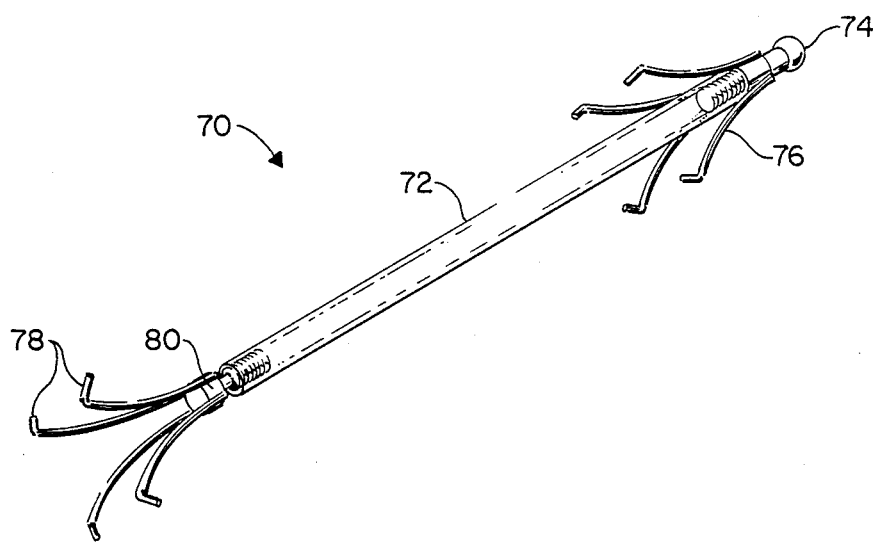

FIG. 6 depicts still another embodiment of the implant capsule of the present invention, generally designated 70. Implant capsule 70 is designed to overcome certain limitations of the implant capsules illustrated in FIGS. 1-5. The relatively more rigid implant capsules described above are particularly suitable for point-source radiation to certain locations within a lung but do not lend themselves as well as implant capsule 70 to placement in an area to be irradiated which extends linearly or curvilinearly along a bronchus or around a corner thereof. For these particular types of applications, implant capsule 70 is particularly appropriate since it comprises a linear flexible body member 72, most suitably constructed of a flexible plastic, which defines a singular chamber therein for receiving a linear array of radioisotope seeds. A sphere 74 with radially extending arms 76 secured thereto (to facilitate grasping of the sphere by forceps 34) is attached to one end of linear body member 72, and arm members 78 secured to stem 80 are attached at the other end thereof to engage the bronchus wall. It should be observed that the hooks of arm members 76 extend inwardly in order to allow catheter 36 to extend thereover and slidably receive implant capsule 70 therein for placement or removal from a selected location in a lung. It should also be noted that the small diameter of implant capsule 70 can permit insertion directly through the bronchoscope without the requirement of retrograde loading as for capsules described hereinbefore.

Although the implant capsules of the present invention have been discussed primarily in terms of a containment vessel for radioisotope seeds, chemotherapeutic agents, as noted hereinbefore, are also contemplated to be placed therein for localized or topical chemotherapy treatment. Though not illustrated in the drawings, the chemotherapeutic agent could be placed within an implant capsule of the present invention and released through a contact wick system, semi-permeable membrane or the like into adjacent tissue.

It will be understood that various details of the invention may be changed without departing from the scope of the invention. Furthermore, the foregoing description is for the purpose of illustration only, and not for the purpose of limitation -- the invention being defined by the claims.

What is claimed is:

1. A device for applying a therapeutic treatment to a selected portion of a body for a predetermined period of time comprising:
    a body member defining at least two elongate therapeutic treatment material receiving chamber means for receiving a radiotherapy treatment agent;
    a plurality of retractable resilient arm members carried by said body member and extending generally radially outwardly therefrom, said arm members being adapted to be compressed radially inwardly into groove means defined by said body member for receiving same during transportation of the device to a portion of the body requiring therapeutic treatment and to then be released so as to allow said arm members to return their position extending outwardly from said body member in order to engage the body portion and to apply the therapeutic treatment thereto; and
    means for attaching an instrument for inserting and removing said device.

2. A device according to claim 1 wherein said body member defines at least two substantially parallel treatment receiving chamber means for receiving said radiotherapy treatment agent.

3. A device according to claim 1, further including a central stem wherein said plurality of resilient arm members extend outwardly from said central stem, said central stem being concentrically secured to said body member and extending substantially parallel to said treatment material receiving chamber means.

4. A device according to claim 3 wherein said plurality of arm members each comprises an end portion turned back on itself to define a barb.

5. A device according to claims 2 or 3 wherein said body member is coextensive with one end of said central stem.

6. A device according to claims 2 or 3 wherein said body member is coextensive with substantially the entire length of said central stem.

7. A device according to claim 1 wherein said body member is adapted to receive one or more radioisotope seeds within each of said at least two therapeutic treatment material receiving chamber means.

8. A device according to claim 1 wherein said body member is adapted to receive a chemotherapeutic agent within each of said at least two therapeutic treatment material receiving chamber means.

9. A device according to claim 1 wherein said body member is adapted to receive a chemotherapeutic agent and a radioactive isotope within said at least two therapeutic treatment material receiving chamber means.

* * * * *